(12) United States Patent
Roorda

(10) Patent No.: US 9,724,184 B2
(45) Date of Patent: Aug. 8, 2017

(54) FILTER WITH DEPLOYABLE ANCHORS

(71) Applicant: Abbott Cardiovascular Systems, Inc., Santa Clara, CA (US)

(72) Inventor: Wouter E. Roorda, Palo Alto, CA (US)

(73) Assignee: ABBOTT CARDIOVASCULAR SYSTEMS, INC., Santa Clara, CA (US)

( * ) Notice: Subject to any disclaimer, the term of this patent is extended or adjusted under 35 U.S.C. 154(b) by 866 days.

(21) Appl. No.: 13/801,866

(22) Filed: Mar. 13, 2013

(65) Prior Publication Data

US 2014/0277077 A1 Sep. 18, 2014

(51) Int. Cl.
*A61M 29/00* (2006.01)
*A61F 2/01* (2006.01)
(Continued)

(52) U.S. Cl.
CPC ............. *A61F 2/01* (2013.01); *A61F 2/848* (2013.01); *A61F 2002/016* (2013.01);
(Continued)

(58) Field of Classification Search
CPC .... A61F 2/01; A61F 2/013; A61F 2/06; A61F 2/064; A61F 2/82; A61F 2/848; A61F 2002/011; A61F 2002/015; A61F 2002/016; A61F 2002/068; A61F 2002/0835; A61F 2002/8483; A61F 2002/8486; A61F 2220/00; A61F 2220/0008; A61F 2220/0016; A61F 2220/0033; A61F 2220/0083; A61F 2250/0004; A61F 2250/0006; A61F 2250/0008; A61F 2250/0012; A61F 2250/0029; A61F 2250/0042; A61F 2250/0059; A61F 2250/0065; A61F 2/02; A61F 2/04; A61F 2/852; A61F 2002/018; A61F 2002/065; A61F 2210/0014; A61F 2210/0019; A61F 2210/0023; A61F 2220/0025; A61F 2220/0041; A61F 2220/0091; A61F 2230/006; A61F 2230/0063; A61F 2230/0086; A61F 2230/0093; A61F 2250/0007; A61F 2250/0009; A61F 2250/001; A61F 2250/0018; A61F 2250/0036; A61F 2250/0037; A61F 2250/0039

See application file for complete search history.

(56) References Cited

U.S. PATENT DOCUMENTS

| 2004/0215212 | A1* | 10/2004 | Teague | A61B 17/221 606/127 |
| 2009/0005803 | A1* | 1/2009 | Batiste | A61F 2/01 606/200 |
| 2012/0245619 | A1* | 9/2012 | Guest | A61F 2/01 606/200 |

OTHER PUBLICATIONS

The Free Dictionary, Bias, 2016,TheFreeDictionary.com.*

* cited by examiner

Primary Examiner — Jonathan Miles
Assistant Examiner — Kendra Obu
(74) Attorney, Agent, or Firm — Workman Nydegger; Ron Devore

(57) ABSTRACT

An implantable and removable filter that may be implanted in and/or removed from a body lumen, such as the Vena Cava. The filter including tissue anchors on expandable anchoring legs, which can be selectively moved between a non-anchoring or pre-deployed configuration into an anchoring or deployed configuration by obturators that are movable inside the anchoring legs.

10 Claims, 15 Drawing Sheets

(51) Int. Cl.
*A61F 2/848* (2013.01)
*A61F 2/08* (2006.01)
(52) U.S. Cl.
CPC .............. *A61F 2002/0835* (2013.01); *A61F 2002/8486* (2013.01); *A61F 2230/006* (2013.01); *A61F 2230/0063* (2013.01); *A61F 2230/0086* (2013.01); *A61F 2230/0093* (2013.01); *A61F 2250/0007* (2013.01); *A61F 2250/0065* (2013.01)

FILTER WITH DEPLOYABLE ANCHORS

BACKGROUND OF THE INVENTION

1. The Field of the Invention

The invention generally relates to the field of temporarily implantable blood filters for prevention of pulmonary embolism.

2. Background and Relevant Art

Pulmonary embolism (PE) oftentimes can cause hospital deaths, which may be preventable. PE is responsible for an estimated 100,000 fatalities in USA every year. PE is typically caused by an embolization of the pulmonary artery, which can lead to right cardiac ventricular overload and acute heart failure. Frequently, the underlying cause is migration of a fragment of clot, originating from a vein in one of the legs, which reaches the pulmonary artery through the Vena Cava. In less frequent cases, other emboli like fragments of fatty tissue have been observed.

The pulmonary circulation is equipped to handle clot fragments of a certain size through thrombolysis, but generally fragments of more than 5 mm in diameter are considered a risk factor for PE. Frequently, patients may be at transient risk for PE, for instance, during the treatment of certain cancers or after orthopedic surgery. In such cases, a temporary implantation of a blood filter, such as a Vena Cava filter, has been shown to lead to a dramatic reduction in the incidents of PE. Typically, such blood filters are umbrella or cage-like structures, designed for temporary implantation, and with the ability to filter emboli greater than a certain cut-off size. Normally, the blood filter is percutaneously implanted and removed with delivery and retrieval catheters.

One of the challenges of typical Vena Cava filters is combining secure anchoring of the device in the implantation phase with reliable retrievability after the at-risk period has passed. In some instances, blood filters have hollow filter legs containing deployable anchor wires. Upon insertion of the catheter and positioning of the device, the filter is advanced out of the catheter to allow the hollow legs to expand and position themselves against the vessel wall. Next, the anchor wires are advanced out of the hollow legs. A preset curvature allows the anchor wires to assume an anchoring configuration, which enables the user to use the anchor wires to engage the vessel wall. Retrieval of the blood filter is achieved by performing the procedure in the reverse order. In this configuration, the thickness of the anchor wires is limited by the size of the hollow legs, and the location of the anchor wires is limited to the distal end of the hollow legs.

The Vena Cava is a notoriously mobile organ. Thus, preventing migration of the blood filter away from the site of implantation and preventing misalignment of the blood filter from tilt-and-shift events remains one of the challenges of Vena Cava filter design. Particularly, anchoring the blood filter with aggressive tissue anchors is limited by the need of reliable retrieval of the blood filter. As complications may occur during the retrieval of the blood filter, in many cases the risk of retrieval may be higher than the risk of leaving the blood filter in place. Accordingly, there are a number of disadvantages in blood filter design that can be addressed.

BRIEF SUMMARY OF THE INVENTION

Accordingly, embodiments of the present invention involve an implantable and retrievable filter for use in a body lumen. The filter can include one or more first anchoring legs having a pre-deployed, non-anchoring configuration, and a deployed, anchoring configuration. Each of the one or more first anchoring legs in the deployed, anchoring configuration may have a first anchor sized and configured to anchor the filter within the body lumen. Additionally, the filter may include one or more first obturators movable inside the one or more first anchoring legs from a first position to a second position. Furthermore, the one or more first anchoring legs may be in the pre-deployed non-anchoring configuration when the one or more first obturators are in the first position. Similarly, the one or more first anchoring legs may be in the deployed, anchoring configuration when the one or more first obturators are in the second position.

Accordingly, embodiments of the present invention involve an implantable and retrievable filter for use in a body lumen. The filter can include one or more first anchoring legs having a pre-deployed, non-anchoring configuration and a deployed, anchoring configuration. Additionally, the filter may include one or more first obturators movable inside the one or more first anchoring legs to reconfigure the one or more first anchoring legs between the pre-deployed, non-anchoring configuration and the deployed, anchoring configuration Embodiments of the present invention also may include a filtering system for deployment in a body lumen. Such system may have a filter that includes at least one anchoring leg reconfigurable between a pre-deployed, non-anchoring configuration, and a deployed, anchoring configuration. The system also may have a catheter that includes an outer sheath and one or more inner members coupled to one or more of the at least one anchoring leg and the at least one obturator. The one or more inner members may be movable to reconfigure the filter between the pre-deployed, non-anchoring configuration, and the deployed, anchoring configuration.

Embodiments described herein also may involve a method of removably implanting a filter in a body lumen. Such the method may include positioning the filter inside the body lumen and reconfiguring one or more anchoring legs into a deployed configuration, each of the one or more anchoring legs forming one or more anchors that engage the anchoring legs with a wall of the body lumen.

Additional features and advantages of exemplary implementations of the invention will be set forth in the description which follows, and in part will be obvious from the description, or may be learned by the practice of such exemplary implementations. The features and advantages of such implementations may be realized and obtained by means of the instruments and combinations particularly pointed out in the appended claims. These and other features will become more fully apparent from the following description and appended claims, or may be learned by the practice of such exemplary implementations as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. For better understanding, the like elements have been designated by like reference numbers throughout the various accompanying figures. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE INVENTION

Glossary

The terms distal end and distal direction refer to an orientation away from the operator.

The terms proximal end and proximal direction refer to an orientation towards the operator.

An obturator in this disclosure is an elongated (e.g., cylindrical) structure, movable inside another elongated structure.

Emboli are solid object floating in the blood stream that can cause obstructions, like blood clots, debris from vascular plaque and particulates or globules of fat.

Disclosed is an implantable and removable filter, which may be implanted in and/or removed from a body lumen, such as the Vena Cava. According to the present invention, the filter can include tissue anchors on expandable anchoring legs, which can be selectively moved between a retracted, non-anchoring, or pre-deployed configuration and an anchoring or deployed configuration and by obturators. The obturators can be movable inside the expandable anchoring legs. Location of the anchors on the anchoring legs, rather than on internal anchor wires offers several advantages. First, anchoring legs may be tubular structures, which may have an inherent greater strength-to-weight ratio than solid rods, so anchors formed from the anchoring legs can be made stronger than those from internal anchor wires without increasing the weight and/or maneuverability of the device. Second, placing the anchors on the anchoring legs allows the anchors to be positioned not only at the distal ends, but anywhere along the length of the anchoring legs, thereby allowing multiple anchors to be placed on a single leg.

The filter disclosed herein may include a filtering section for capturing emboli and for removably anchoring the filter to the vessel wall, and an operator section for delivering the filter into a body lumen and/or retrieving the filter therefrom. In some embodiments, the operator section also may be used to deploy or expand the anchors into a deployed configuration. The operator section also may be user to collapse and/or retract the anchors into a pre-deployed configuration. It should be understood that, while some of the embodiments in this disclosure are discussed as having distinct filtering and operator sections, in other embodiments various levels of integration between the filtering and operator sections may be present. As such, physical separation or differentiation between the filtering and operator sections may not be present in every embodiment of this invention.

Figure 1A:
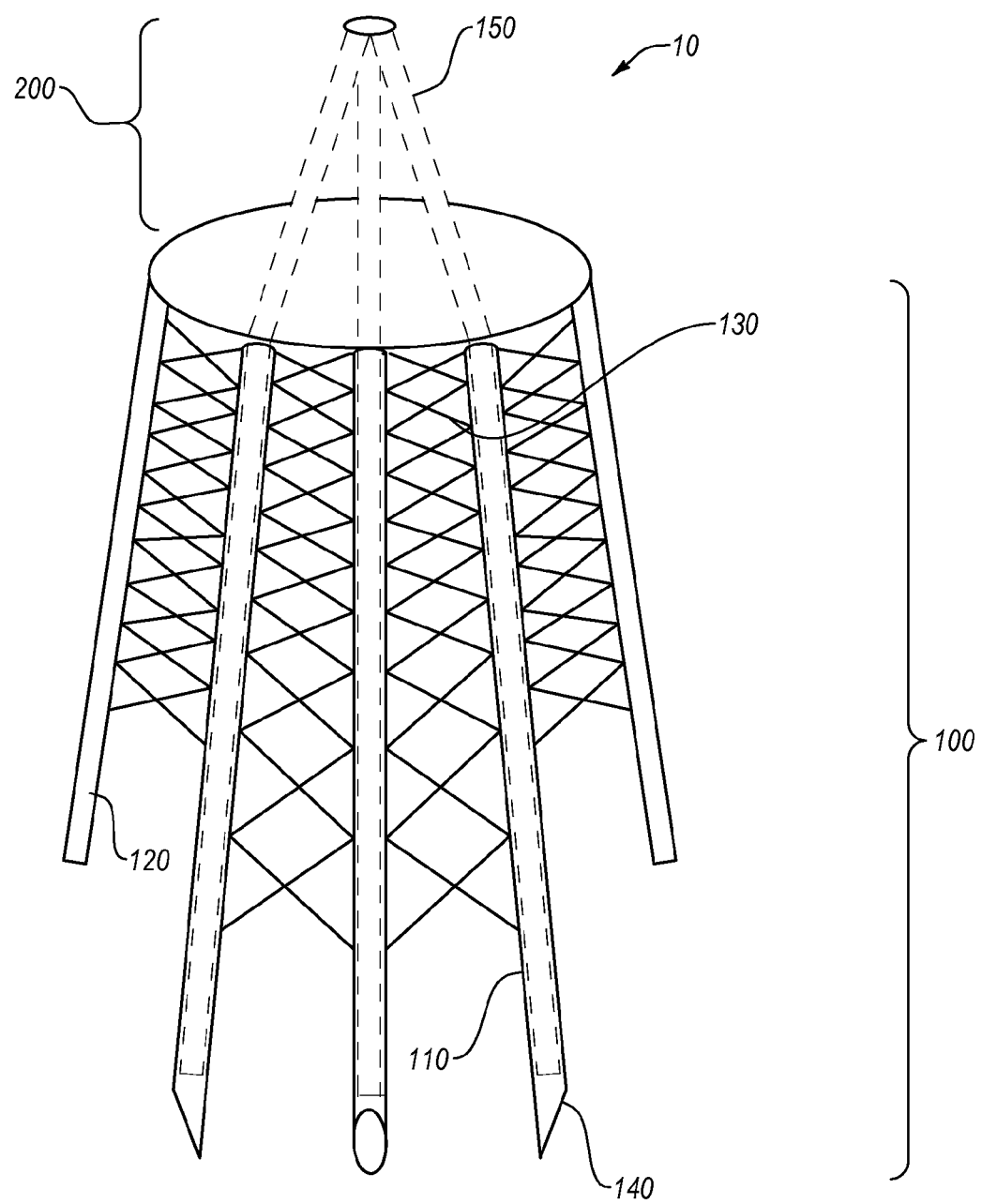
FIG. 1A illustrates a cross-sectional view of a filter in a pre-deployed configuration in accordance with one embodiment of the present invention.

FIG. 1A shows one embodiment of a filter 10 in a pre-deployed configuration. Particularly, the filter 10 includes a filtering section 100 and an operator section 200. The filtering section 100 may include a number of elongated members separated from each other in a manner that allows the filter 10 to capture emboli above a predetermined size. For example, elongated members can be positioned circumferentially about an axis of the filter 10, and can be spaced apart from each other by predetermined distances (e.g., by distances less than the predetermined emboli size).

In some embodiments, the elongated members of the filter 10 can include anchoring legs 110, which can secure the filter 10 to the body lumen. The anchoring legs can incorporate one or more anchors 140 that can engage the wall of the body lumen. It should be appreciated that, in FIG. 1A, the anchors 140 are illustrated in the pre-deployed configuration. Particularly, the shape of the anchors 140 in the pre-deployed configuration may be different from the anchors in the deployed configuration.

In addition, in some embodiments, the filter 10 can include an operator section 200 that can reconfigure the filter 10 from the pre-deployed configuration into a deployed configuration. In particular, the operator section 200 can be used to manipulate the anchor legs 110 and/or the anchors 140 in a manner that engages the anchors 140 with the wall of the body lumen, as described below in further detail. In other words, the operator section 200 can reconfigure the anchoring legs 110 and/or the anchors 140 from a pre-deployed configuration into a deployed configuration and vice versa.

In additional or alternative embodiments, the filter 10 also can include structural members 130, which can be positioned between the elongated members of the filtering section 100. For example, the structural members 130 can be located between the anchor legs 110. In some instances, the structural members 130 also can couple the anchor legs 110 together. The structural member 130 also can provide rigidity and/or improved stability of the filter 10 in the deployed and/or in the pre-deployed configurations. Furthermore, the structural members 130 can filter emboli of predetermined sizes (e.g., sizes greater than the spacing between the structural members 130).

Additionally or alternatively, the structural members 130 can contribute to the filtering capacity of the filter 10. The structural members 130 can be tubular or solid, and may have various cross-sectional geometries. For instance, the structural members 130 may be solid, elongated cylinders with a circular cross-section. In some embodiments, the structural members 130 also may have a substantially linear configuration. Alternatively, the structural members 130 can have other geometries, such as curved, spiral, or undulating geometries.

In at least one embodiment, the anchoring legs 110 are hollow, tubular structures. Furthermore, as noted above, arrangements of the anchoring legs 110 in the filtering section 100 can provide filtering of the emboli in addition to structural support and/or stability. The anchoring legs 110 can have any suitable cross-sectional shape, which can vary from one embodiment to another. In one or more embodiments, the shape of the cross-section of the anchoring legs 110 may be circular, but can be any desired geometry, including oval, triangular, rectangular, or more complex geometries. As described below, the anchoring legs 110 can be actuated by corresponding obturators 150. For example, the obturators 150 can be manipulated at and/or secured to the operator section 200. Accordingly, the user of the filter 10 can, for instance, move the operator section 200 to manipulate the obturators, which, in turn, can actuate the anchoring legs 150 and reconfigure the filter 10 into the deployed configuration.

In one embodiment, the obturators 150 can move within the hollow anchoring legs 110 (e.g., in the proximal and/or distal direction). Such movement of the obturators 150 can engage the anchoring legs 110 with the wall of the body lumen. For instance, the obturators 150 can be withdrawn from the anchoring legs 110, thereby reconfiguring the anchoring legs into a deployed configuration, as described below in further detail.

In additional or alternative embodiments, the elongated members of the filtering section 100 can include one or more positioning legs 120 that can provide further structural support and filtering capacity to the filter. Similar to the anchoring legs 110, the positioning legs 120 also can be tubular or solid, and can have various cross-sectional geometries. In some cases, a preferred structure of the positioning legs 120 may be solid, elongated cylinders with a circular diameter.

The anchoring legs 110 and positioning legs 120, in their expanded or deployed configuration, may extend radially outward from a central axis of the filter 10. In one embodiment, in the deployed or in the pre-deployed configuration, the anchoring legs 110 and/or the positioning legs 120 may be positioned at a similar or identical angle relative to the center axis of the filter 10. Alternatively, the anchoring legs 110 and/or the positioning legs 120 may be positioned at different angles relative to the center axis of the filter 10.

In the embodiment shown in FIG. 1A the anchoring legs 110 and positioning legs 120 extend from a location near the center axis of the device. In other embodiments, the anchoring legs 110 and/or the positioning legs 120 may originate from other locations. As discussed in further detail below, it is possible to link at least some of the anchoring legs 110 and/or positioning legs 120 to locations near the center axis in an indirect manner (e.g., by coupling the anchoring legs 110 and/or positioning legs 120 to another member, such as a hub, which may be located near the center axis).

The filter 10 can incorporate any number of anchoring legs 110, which may vary from one embodiment to the next. In one example, the filter 10 includes three anchoring legs 110; however, this disclosure is not so limited. Hence, in one or more other embodiments, the filter 10 can include as few as a single anchoring leg 110 or as many as may be suitable for a particular application.

Figure 1B:
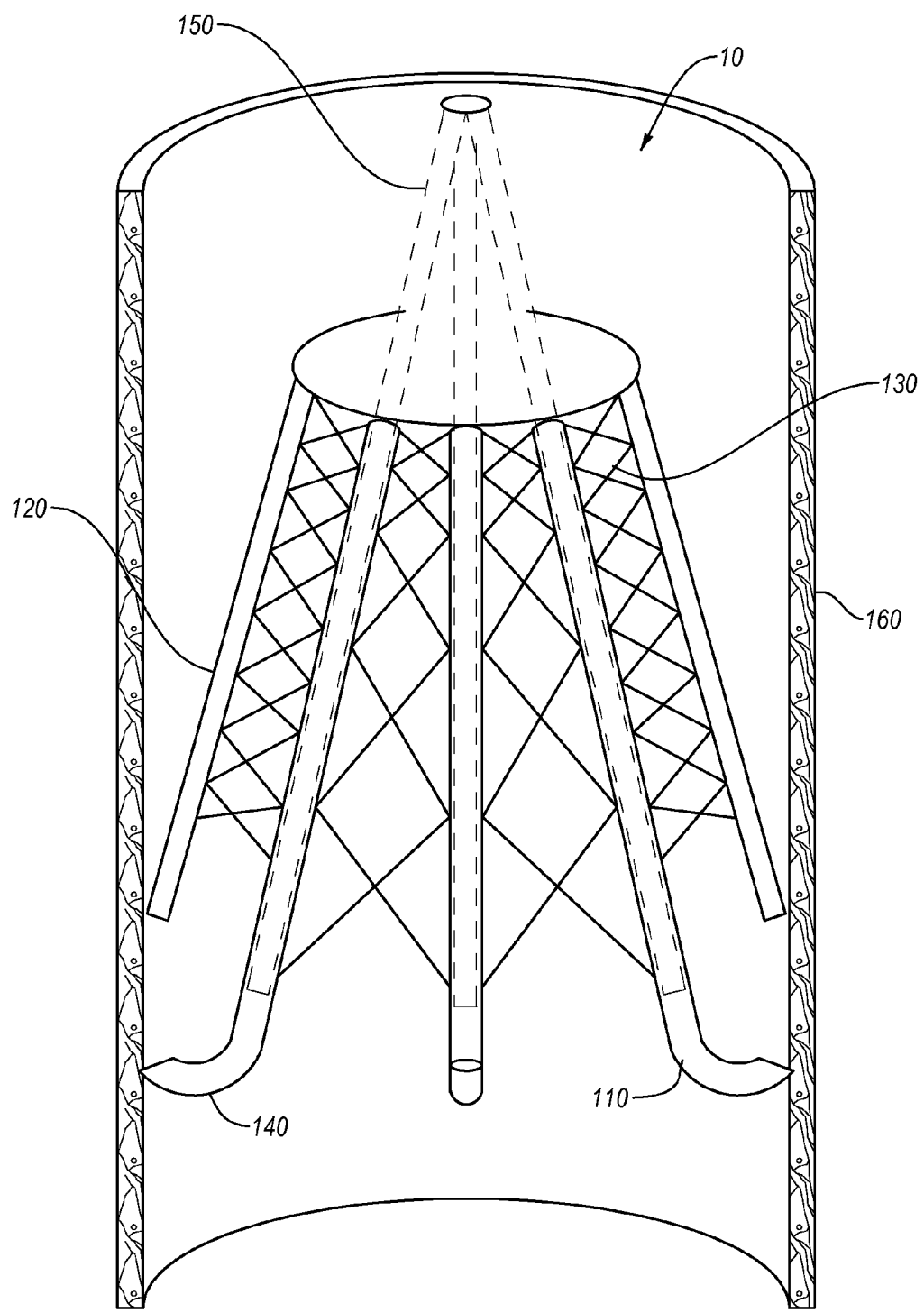
FIG. 1B illustrates a cross-sectional view of the filter of FIG. 1B in a deployed configuration in accordance with one embodiment of the present invention.

In any event, the anchoring legs 110 and/or the positioning legs 120 can be actuated and reconfigured from a pre-deployed configuration to a deployed configuration. For instance, FIG. 1B illustrates one embodiment of the filter 10 in the deployed configuration. Specifically, the obturators 150 can be moved within the anchoring legs 110, thereby reconfiguring the anchoring legs 110 from the pre-deployed configuration (FIG. 1A) into the deployed configuration (FIG. 1B). As described below, the anchoring legs 110 can comprise a memory shape alloy, which can allow the anchors 140 to be reconfigured into the deployed, hook-like configuration after at least partial removal or withdrawal of the obturators from the anchoring legs 110.

Accordingly, the anchors 140 of the anchoring legs 110 can engage a wall of a body lumen 160. Specifically, as the anchors 140 are reconfigured into the deployed configuration, the hooks formed by the anchors 140 in such configuration can hook into the wall of the body lumen 160, thereby securing the filter 10 in the body lumen 160. Conversely, the anchors 140 also can be reconfigured into the pre-deployed configuration, to allow the filter 10 to be unhooked and removed from the body lumen 160. For instance, the obturators 150 can be advanced into the anchoring legs 110 in a manner that reconfigures the anchors 140 into the pre-deployed configuration, thereby releasing the anchors 140 from the wall of the body lumen 160. Thereafter, the filter 10 can be removed from the body lumen 160.

The materials included in the filter 10 may provide properties like biocompatibility, sterilizability, physical and chemical stability, strength and flexibility. In some instances, metals and metal alloys may be preferable over polymeric materials. Suitable materials may include stainless steel, titanium, Elgiloy and nitinol. In one embodiment, the anchoring legs 110 may comprise nitinol, while the obturators 150 may comprise stainless steel. It should be appreciated, however, that the filter 10 can include any number of suitable materials, which may vary from one embodiment to another.

In preferred embodiments of the device, the flexibility of the materials allows the filter 10 to be delivered through a delivery sheath of approximately 10 F diameter. Subsequently, the filter 10 can be expanded to fit into and/or be secured within a body lumen, such as a vena cava of at least 30 mm diameter. Likewise, the filter 10 can be collapsed back into the delivery sheath, as described below in further detail, and may be retrieved from the body lumen. The anchoring legs 110, positioning legs 120, and structural members 130 may be coupled together in various configurations or patterns that may provide a filtering capacity for capturing emboli migrating in a blood vessel when the filter is in the deployed configuration. Also, in some examples, in the deployed configuration, the filter 10 may define or form a cone-shaped structure or a cage-type structure. For instance, the anchoring legs 110 and/or the positioning legs 120 may be positioned and oriented at a non-parallel angle relative to the center axis of the filter 10, in a manner that forms a cone. Moreover, as noted above, the structural members 130 may interconnect some or all of the anchoring legs 110 and/or positioning legs 120, thereby providing additional filtering capability as well as structural support for the filter 10.

As noted above, the elongated members, such as the anchoring legs 110 and positioning legs 120 can be coupled together around the center axis of the filter 10. Particularly, the elongated members can be coupled directly to each other. Alternatively, the elongated members of the filter 10 can be coupled together indirectly. For instance, the elongated members of the filter 10 can be coupled to a common hub, as described below. In the context of this disclosure, the term coupled to each other refers to both direct and indirect connections.

The obturators 150 also can be coupled together. In some instances, the obturators 150 can be directly coupled together around the center axis of the filter 10. In additional or alternative embodiments, the filter 10 can include obturators 150 that are indirectly coupled together. For example, the obturators 150 can be coupled to a hub, as described below.

In one embodiment, the anchoring legs 110 are involved in capturing emboli. In other words, the anchoring legs 110 can be incorporated into the filtering portion 100 of the filter 10 and may form or define a part of the filtering portion 100 that performs the filtering functions (i.e., capturing emboli). In alternative embodiments, however, the anchoring legs 110 may be uninvolved in the filtering function of the filter 10 (e.g., the anchoring legs 110 may only provide structural support for and/or anchoring of the filter). For example, FIGS. 2A-2B illustrate embodiments of the filter that include anchoring member that are substantially uninvolved in the filtering function of the filter.

Figure 2A:
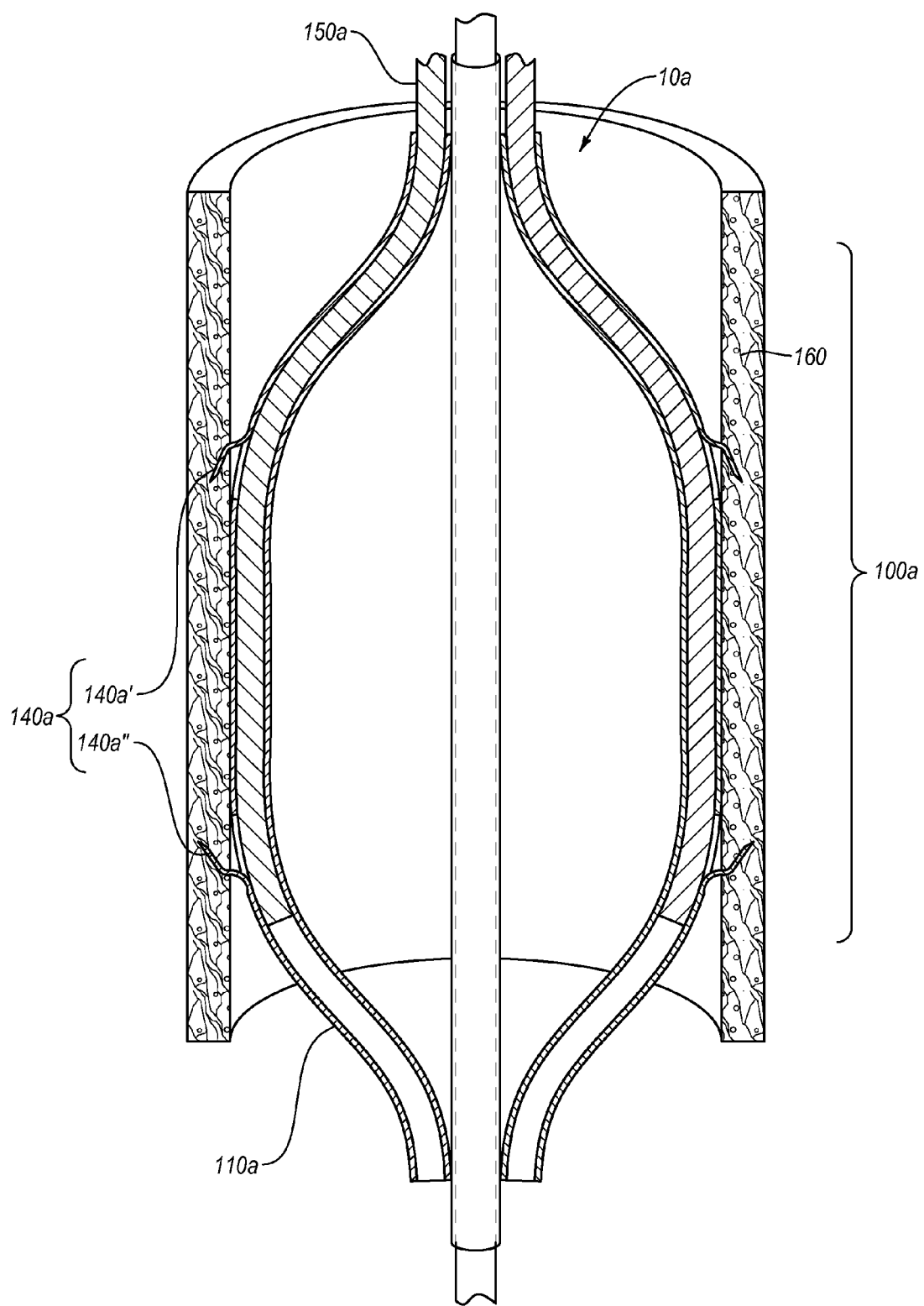
FIG. 2A illustrates a cross-sectional view of a filter in accordance with another embodiment of the present invention.
Figure 2B:
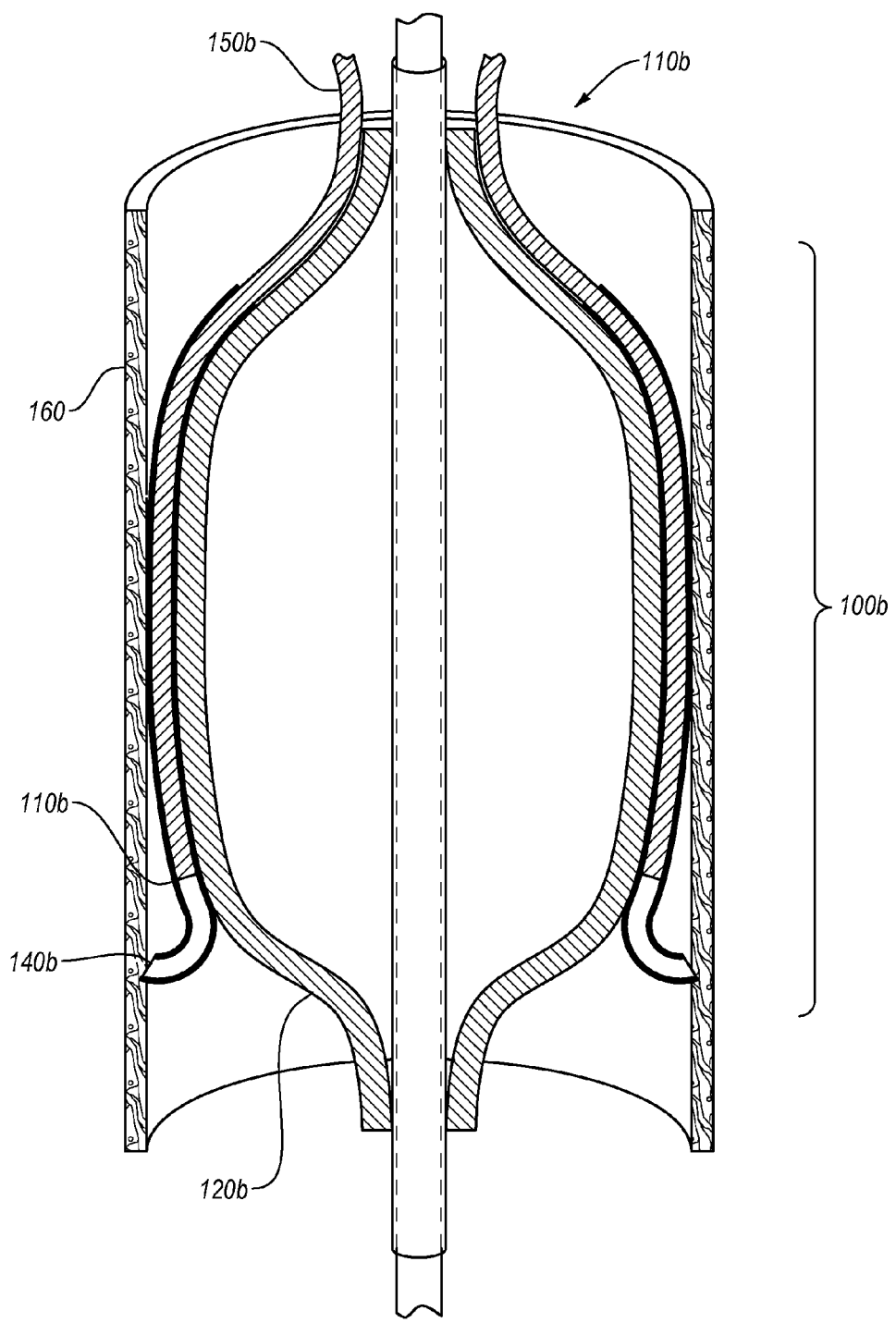
FIG. 2B illustrates a cross-sectional view of a filter in accordance with yet another embodiment of the present invention.

Particularly, FIG. 2A illustrates a filter 10a that has a filtering section 100a that includes multiple elongated members. Except as otherwise described herein, the filter 10a and its components and elements can be similar to or the same as the filter 10 (FIGS. 1A-1B) and its respective components and elements. In at least one embodiment, the filtering section 100a may be a cage-type structure. As noted above in connection with the filtering section 100 (FIGS. 1A-1B), the filtering section 100a can filter emboli of predetermined sizes or size ranges.

In some embodiments, the elongated members of the filtering section 100a may include only anchoring legs 110a. In one or more embodiments, the filtering section 100a may include other elongated members, such as positioning members. Moreover, the filtering section 100a also may include structural members, which may couple to and/or interconnect with the elongated members, such as with the anchoring legs 110a and/or with the positioning legs, of the filtering section 100a.

Also, in one embodiment, the anchoring legs 110a may be coupled at distal and proximal ends of the filtering section 100a. In some instance, such coupling of the anchoring legs 110a may form a cage-type structure, which may include a hollow, enclosed space in the center thereof.

The filter 10a also can include anchors 140a (e.g., anchors 140a', 140"), which can secure the filter 10a to and/or within the body lumen 160. The anchors 140a may be positioned at one or several locations along the anchoring legs 110a. It should be appreciated that the anchors 140a may positioned at any number of suitable locations on the anchoring legs 110a and may have any number of suitable orientations, which can allow the anchors 140a to engage the wall of the body lumen 160. For instance, the anchors 140a may be located near distal and proximal ends of the filtering section 100a.

Similar to the filter 10 (FIGS. 1A-1B), the filter 10a can include obturators 150a, which can reconfigure the filter 10a from a pre-deployed configuration to a deployed configuration (shown in FIG. 2A) and vice versa. For example, the obturators 150a can slide or move within the anchoring legs 110a, thereby causing the anchoring legs 110a to transform from the pre-deployed configuration to the deployed configuration and vice versa.

In one example, the anchors 140a can be partial cutaway sections in the wall of the anchoring legs 110a. Thus, positioning the obturators 150b in a first position can push the anchors 140a away from the remaining portion of the anchoring leg 110a, in a manner that the anchors 140a engage the wall of the body lumen 160. As such, the filter 10a can be in the deployed configuration when the obturators are positioned in the first position.

Conversely, the obturators also can be positioned at a second position, for instance, such that the anchors 140a can move back to their respective pre-deployed positions or configurations, thereby releasing the filter 10a from the wall of the body lumen 160. Accordingly, manipulating the obturators between the first and second positions can reconfigure the filter 10a into the deployed position (i.e., engaging the anchors 140a with the wall of the body lumen 160) and into the pre-deployed position (i.e., disengaging anchors 140a and/or allowing the anchors 140a to disengage from the wall of the body lumen 160).

As mentioned above, in addition to or in lieu of the anchoring legs, the filter also can include positioning legs. For instance, FIG. 2B illustrates a filter 10b, which includes a filtering section 100b that has anchoring legs 110b coupled to positioning legs 120b. Except as otherwise described herein, the filter 10b and its components and elements can be similar to or the same as any of the filters described herein, including filters 10, 10a (FIGS. 1A-2A) and their respective components and elements.

In some embodiments, the positioning legs 120b may be coupled together at distal and proximal ends of the filtering section 100b of the filter 10b. Accordingly, the positioning legs 120 can expand the filtering section 100b into an expanded configuration, thereby reconfiguring the filter 10b into a partially-deployed configuration, where the filter 10b is positioned in the body lumen and has the anchoring legs 110b and/or positioning legs 120b near or abutting the wall of the body lumen, but the anchoring legs 110b are not engaged therewith (i.e., not anchored thereto). After the filtering section 100b is expanded, the anchoring legs 110b can be reconfigured into a deployed configuration. As noted above, the anchoring legs 110b can include one or more anchors 140b, which can secure the filter 10b to the wall of the body lumen 160.

More specifically, the filter 10b can include obturators 150b, which can move within the anchoring legs 110b from a first position to a second position. For instance, moving the obturators into the first position can engage the anchors 140*b* with the wall of the body lumen 160, while moving the obturators into the second position can disengage the anchors 140*b* from the wall of the body lumen 160.

In some embodiments, the anchoring legs 110*b* can provide structural support and/or can anchor the filter 10*b* to and/or within the body lumen 160 without providing any filtering functionality of the filter 10*b*. Hence, in at least one embodiment, the positioning legs 120*b* and/or the obturators 150*b* may perform the filtering function. Alternatively or additionally, the filtering section 100*b* may include the structural members (not shown), which may cooperate with the anchoring legs 110*b*, positioning legs 120, obturators 150*b*, or combinations thereof to filter emboli.

As mentioned above, the anchoring legs 110*b* can maintain the filter 10*b* in a fixed location, typically infra-renal in the Vena Cava, and in a fixed orientation, typically coaxial with the Vena Cava. To provide secure location and orientation of the filter 10*b*, one or more of the anchoring legs 110*b* may contain at least one deployable and retractable anchor 140*b*. In the context of this disclosure the deployed configuration of the anchors 140*b* refers to their anchoring position, while the retracted configuration refers to their non-anchoring position.

In some embodiments, a single anchoring leg 110*b* with a single anchor 140*b* (e.g., a sufficiently large anchor 140*b*) may be capable of maintaining the filter location. Also, the orientation of the filter 10*b* can be maintained by the design of the anchoring and positioning legs, for instance by including a cylindrical or cage-like section abutting the venous wall. As described above, such cylindrical and/or cage-like section can be the filtering section 100*b*.

In practice, the Vena Cava is a highly mobile organ and prevention of filter movement and migration is one of the greatest challenges in filter design. As a consequence, multiple anchors 140*b* may be preferable to secure the filter 10*b* in place. In some instances, a minimum number of points required to define a cross-sectional plane through the Vena Cava is three. Consequently, the preferred minimum number of anchoring points defining the orientation of the filter also can be three. Thus, it should be appreciated that the number of anchors 140*b* may vary from one embodiment to the next. Additional or alternative considerations may include the need for redundancy, a preference for a larger number of small anchors instead of a small number of large anchors to reduce local injury etc., which also may dictate the number of anchors 140*b* incorporated in the filter 10*b*.

Generally, the anchors 140*b* can be placed anywhere along the length of ° the anchoring legs 110*b* where the design of the legs allows them to be in contact with the vessel wall. Thus, the anchors can be located at one or more ends of the anchoring legs 110*b*, along the length of the legs, or in a combination of these two options. Multiple anchors 140*b* can be located on a single anchoring leg 110*b*. When placed at the end of an anchoring leg 110*b*, the anchors 140*b* can be formed by shaping the outer shape of the anchoring leg 110*b* into an anchoring configuration.

The shape of the anchors 140*b* may need to provide adequate tissue purchase, while at the same time allowing the movement of the obturators 150*b*. Shapes without sharp bends allow easier passage of the obturator 150*b* and therefore may be preferred. Acceptable shapes may include, but are not limited to, hooks, barbs, and coils.

In one embodiment, where the anchors are formed at the distal ends of the anchoring legs 110*b*, the anchoring legs 110*b* may be made from a material that has shape memory and, as more fully described below, permits the anchors 140*b* to be selectively moved between a retracted configuration and a deployed configuration and vice versa. Suitable shape memory material may include nitinol of any other known material with the desired properties. In order to facilitate tissue penetration by the anchors during deployment, the tip of the anchors is preferably sharpened. Furthermore, although reference in the above description was made to configurations of the anchoring legs 110*b* and anchors 140*b*, it should be appreciated that such configurations are generally equally applicable to any one of the anchoring legs and anchors described herein.

Figure 3A:
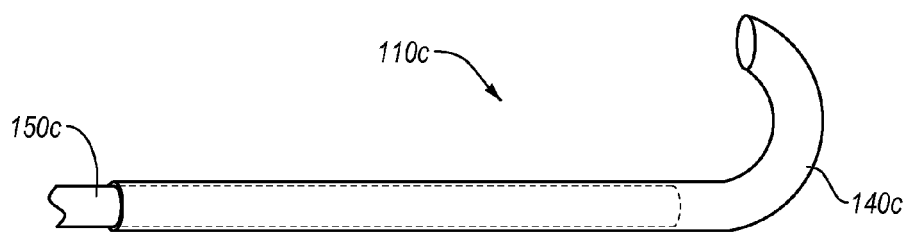
FIG. 3A illustrates a perspective view of an anchoring leg in a deployed configuration in accordance with one embodiment of the present invention.
Figure 3B:
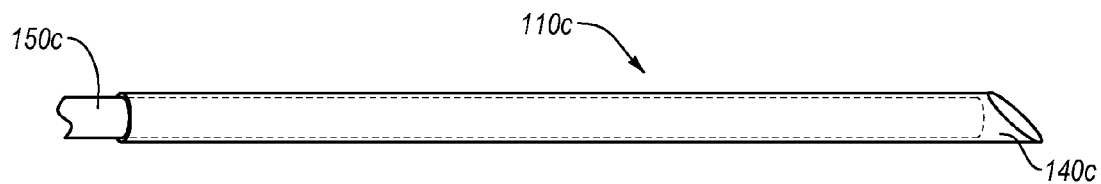
FIG. 3B illustrates a perspective view of the anchoring leg of FIG. 3A in a pre-deployed configuration.

In the case of placement at the end of the leg, the anchors can assume their anchoring configuration in the absence of the obturator. One example of such anchor is illustrated in FIGS. 3A and 3B. More specifically, FIGS. 3A-3B illustrate an anchoring leg 110*c* in a deployed and pre-deployed configurations, respectively. In one embodiment, anchor 140*c* of the anchoring leg 110*c* can be in the shape of a hook. With an obturator 150*c* at a first position, such as partially withdrawn from the anchoring leg 110*c*, proximally relative to the distal end of anchoring leg 110*c*, as illustrated in FIG. 3A, the shape memory of anchoring leg 110*c* causes the distal end of anchoring leg 110*c* to form a hook-shaped anchor 140*c* in its deployed configuration.

FIG. 3B shows the same anchor 140*c* and the anchoring leg 110*c* in a retracted or pre-deployed configuration, after movement of the obturator 150*c* to a second position, such as closed to the distal end of the anchoring leg 110*c*. In such embodiment, distal movement of the obturator 150*c* causes the anchor 140*c* to be reconfigured into the pre-deployed or non-anchoring configuration, while proximal movement of the obturator 150*c* relative to anchoring leg 110*c* causes a deployed or anchoring configuration. The anchor 140*c* may be incorporated into any one of the filters described herein.

When placed along the length of the anchoring leg, the anchors can be formed by cutting a part of the wall of the tube forming the anchoring leg, thereby forming a tab that can be made to move outward from the anchoring leg in response to movement of the obturator. The tab can be shaped in any desired configuration, including square, rectangular, triangular or more complicated geometric shapes. Barbed configurations may allow better tissue purchase, but may cause more tissue damage during removal.

Figure 4A:
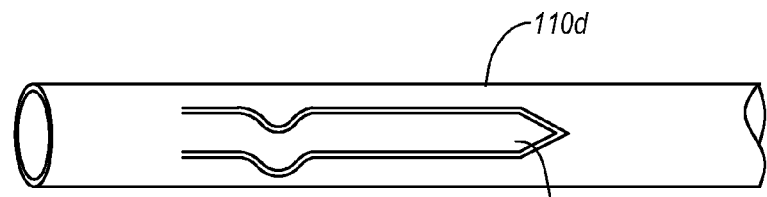
FIG. 4A illustrates a perspective view of an anchoring leg in a pre-deployed configuration in accordance with one or more embodiments of the present invention.
Figure 4B:
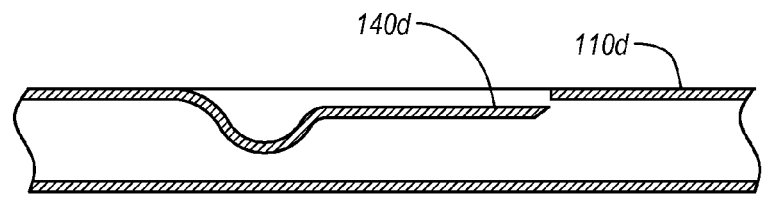
FIG. 4B illustrates a cross-sectional view of the anchoring leg of FIG. 4A.
Figure 4C:
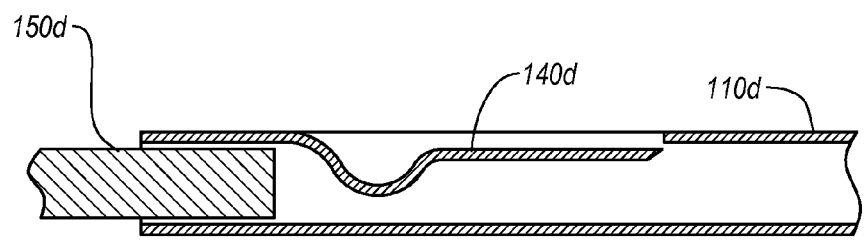
FIG. 4C illustrates a cross-sectional view of the anchoring leg of FIG. 4A with a partially inserted obturator in accordance with an embodiment of the present invention.

When placed along the length of the anchoring leg, the anchors can assume their anchoring or deployed configuration due to the presence of the obturator. FIGS. 4A-4C show an embodiment of an anchoring leg 110*d*, with an anchor 140*d*. Specifically, FIGS. 4A-4B show a perspective view and a cross-sectional view of the anchoring leg 110*d* in a pre-deployed configuration. The anchor 140*d* can comprise a tab or a section of a wall partially cut out of the wall of the anchoring leg 110*d*. Hence, in some embodiments, the anchor 140*d* may be able to flex or move relative to the remaining portion of the wall of the anchoring member 110*d*. Particularly, the anchor 140*d* can move outward into the deployed configuration and can engage the wall of the body lumen.

Figure 4D:
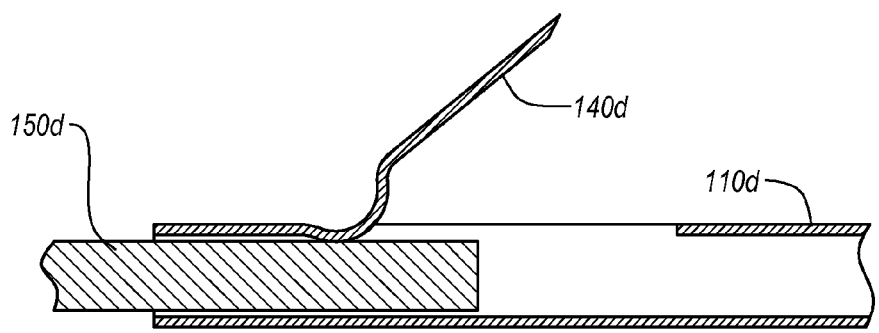
FIG. 4D illustrates a cross-sectional view of the anchoring leg of FIG. 4A in a deployed configuration in accordance with an embodiment of the present invention.

Deployment of the anchors 140*d* by either a distal or proximal movement of the obturator 150 relative to the anchoring leg 110*d* is illustrated in FIGS. 4C-4F. In FIG. 4C, an obturator 150*d* is illustrated partially inserted into the anchoring leg 110*d* before engaging the anchor 140*d*. In FIG. 4D, the obturator 150*d* has been advanced to engage the anchor 140*d*, thereby causing the anchor 140*d* to move or bend outward into the deployed configuration. In one or more embodiments, such bending of the anchor 140*d* can be elastic, such that the anchor 140*d* can be flexed back into the pre-deployed configuration (e.g., when the obturator 150d is removed or disengaged from the anchor 140d). The anchoring leg 110d can be used with or incorporated into any of the filters described herein.

Figure 4E:
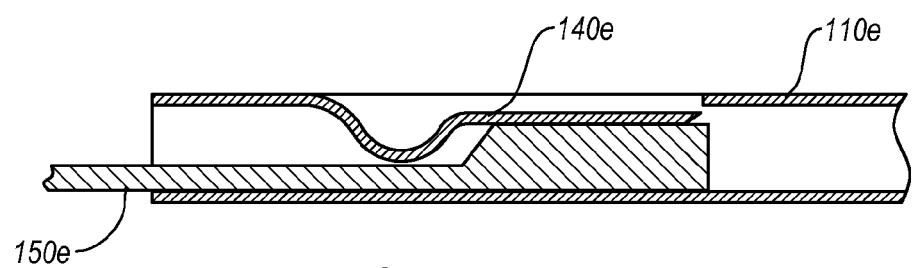
FIG. 4E illustrates a cross-sectional view of an obturator and an anchoring leg in a pre-deployed configuration in accordance with one or more embodiments of the present invention.
Figure 4F:
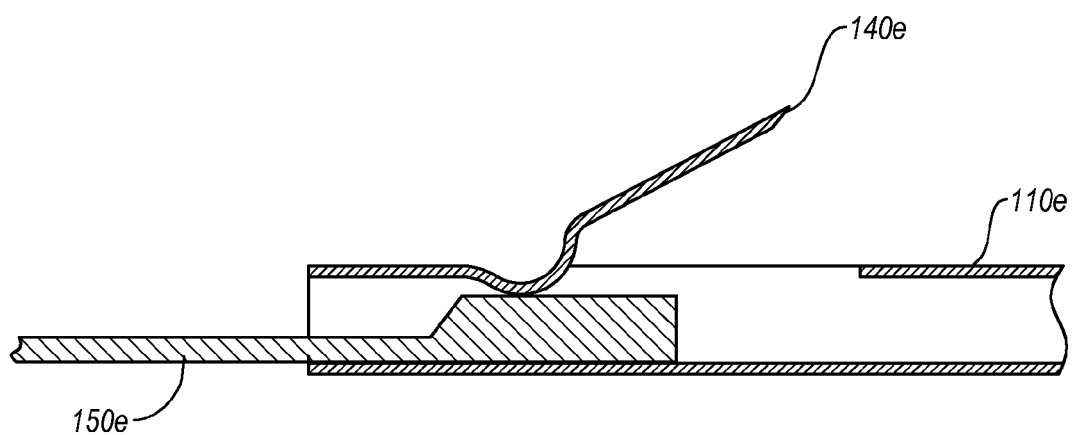
FIG. 4F illustrates a cross-section view of the anchoring leg of FIG. 4E in a deployed configuration in accordance with one or more embodiments of the present invention.

In another embodiment, illustrated in FIGS. 4E-4F, an anchoring leg 110e can include an anchor 140e. Furthermore, an obturator 150a can be moved from the inside of the anchoring leg 110e out to engage and move the anchor 140e outward, into the deployed configuration. Specifically, as illustrated in FIG. 4F, the obturator 150e can be advanced at least partially out of the anchoring leg 110, thereby engaging the anchor 140e, and causing the anchor 140e to flex or bend outward into the deployed configuration. The anchoring leg 110e can be used with and incorporated into any of the filters described herein.

Figure 5A:
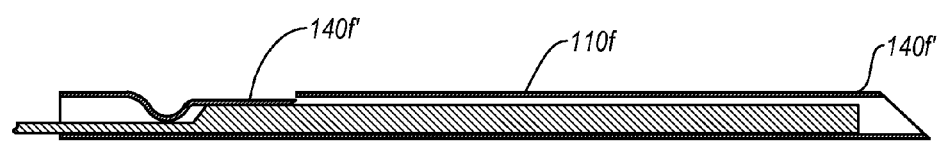
FIG. 5A illustrates a cross-sectional view of an obturator and an anchoring leg in a pre-deployed configuration in accordance with an embodiment of the present invention.
Figure 5B:
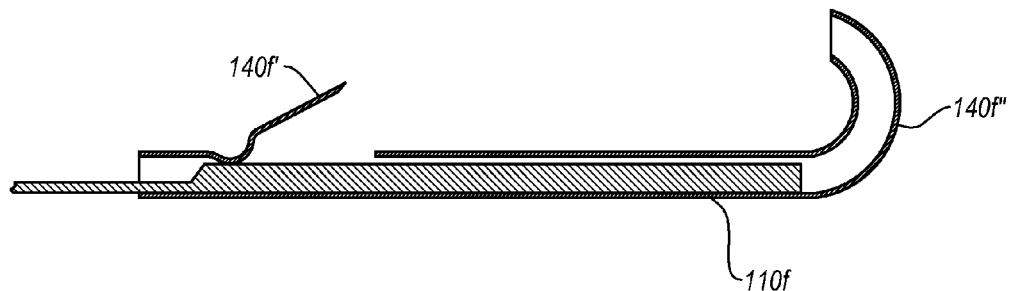
FIG. 5B illustrates a cross-section view of the anchoring leg of FIG. 5A in a deployed configuration in accordance with one or more embodiments of the present invention.

FIGS. 5A and 5B show an embodiment that includes an anchoring leg 110f with multiple anchors thereon. Specifically, the anchoring leg 110f may include a first anchor 140f, which can be located along the length of the anchoring leg 110f, and a second anchor 140f'', which may be located near an end of the anchoring leg 110f. Furthermore, a single obturator 150f can engage and actuate both the first and second anchors 140f, 140f'', thereby reconfiguring the anchoring leg 110f as well as the first and second anchors 140f, 140f'' into the deployed configuration, as shown in FIG. 5B.

Conversely, as illustrated in FIG. 5A, the obturator 150f can be moved to a distal position, causing both first and second anchors 140f and 140f'' to assume a non-anchoring or pre-deployed configuration. In any event, the obturator 150f can be moved inward (or into the anchoring leg 1100 and outward relative to the anchoring leg 110f to engage the first and second anchors 140f, 140f'' and to reconfigure the anchoring leg 110f and the first and second anchors 140f, 140f'' into the pre-deployed and deployed configuration and vice versa.

In some embodiments, the obturator 150f can fit slidably inside the anchoring leg 110f, but can have sufficient stiffness in both the distal and the proximal direction to move the first and second anchors 140f and 140'' between the deployed and pre-deployed configurations. The anchoring legs 110f can be used with and/or incorporated into any one of the filters described herein.

The obturators may include materials that have properties like biocompatibility, sterilizability, stability, strength and flexibility. Many metals, metallic alloys and polymeric materials may have suitable properties. Metals and metal alloys may be preferable over polymeric materials. Among others, suitable materials include stainless steel, titanium, Elgiloy and nitinol. It should be appreciated that any number of suitable materials, alloys, and combinations thereof may be used or included in the obturators.

The structure, material composition, and properties of the obturators may vary or change along the length thereof. Indeed, it may be advantageous to vary the properties along the length of the obturators. For instance, the obturators may have sufficient column strength along most of the length thereof to transfer forces, while at the same time may have the flexibility to accommodate curvatures in the design of the anchoring legs. By contrast, if an obturator is used to straighten an anchor at the distal end of an anchoring leg, the distal tip of the obturator may require additional stiffness. This may be achieved with variously configured obturators, including but not limited to using different designs for the length and the tip of the obturators, such as different diameters or cross-sectional geometries, by the use of different materials for the length and the tip of the obturator, by using different annealing processes for tip and length, and combinations thereof.

If desired, the obturators and/or the anchoring legs can be coated with a biocompatible, lubricious material to facilitate movement of the obturators inside the anchoring legs. Numerous lubricious materials are available, examples of which include fluorinated polymers like Fluorinated Ethylene Propylene (FEP) and Poly Vinylidene Fluoride-Hexafluoropropylene (PVDF-HFP) and non-fluorinated compounds like Parylene. Other potentially beneficial coating materials may include hydrophobic heparin derivatives like Tri Dodecyl Methyl Ammonium Heparin, which may prevent unwanted clot accumulation.

Figure 6A:
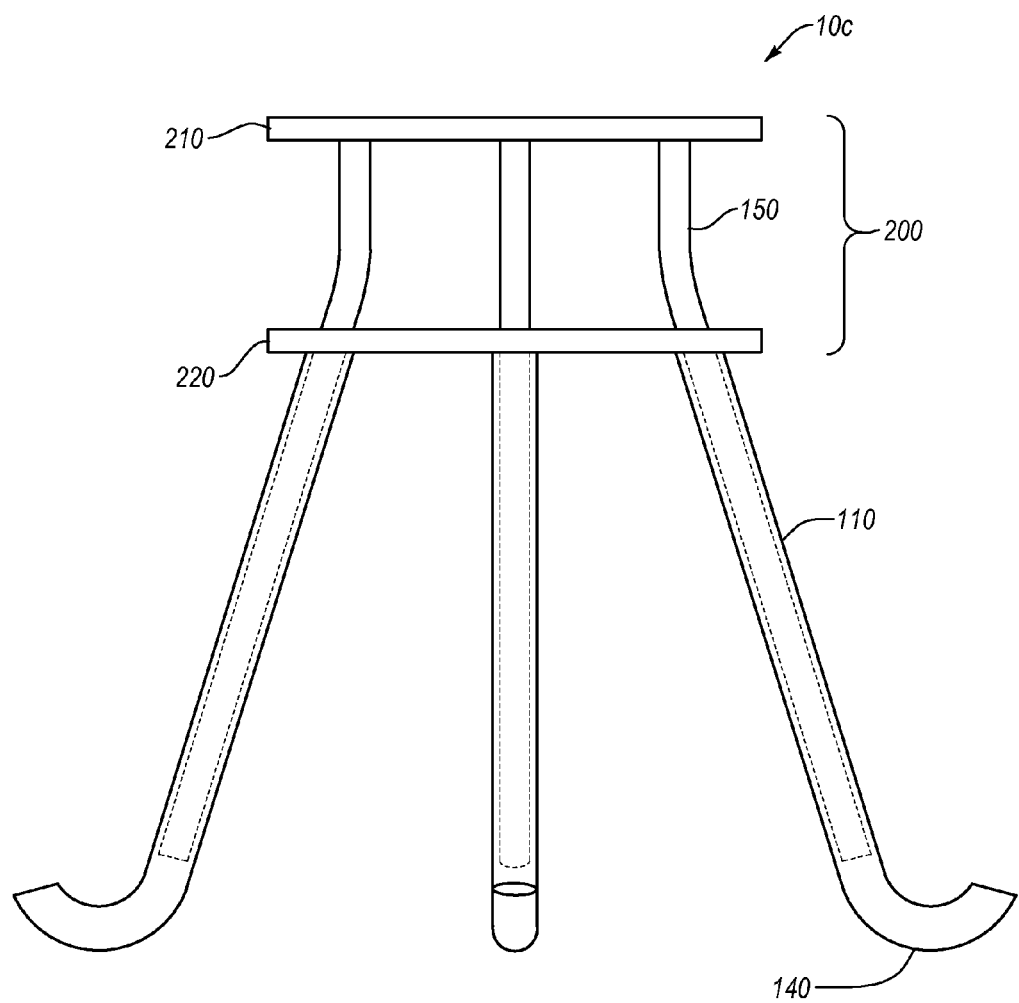
FIG. 6A illustrates a side view of a filter in accordance with an embodiment of the present invention.

To operatively connect the obturators and the anchoring legs, the filter may include a one or more hubs. For instance, a first hub may tie or couple together the individual obturators, while a second hub may tie or couple together the individual anchoring legs. Such hubs can actuate the obturators and/or the anchoring legs in a manner that reconfigures the filter from a pre-deployed configuration to a deployed configuration, and vice versa. FIG. 6A illustrates a filter 10c that includes a first obturator hub 210 and a second obturator hub 220. Except as otherwise described herein, the filter 10c and its components and elements can be similar to or the same as any of the filters 10, 10a, 10b (FIGS. 1A-2B).

In one embodiment, the first and second hubs 210, 220 can be located in the operator section 200 of the filter 10c. In some instances, the operator section can be closer to a proximal end of the filter 10c. Hence, in some embodiments, the first and second hubs 210, 220 can be located near or toward the proximal end of the filter 10c.

In an embodiment, the first hub 210 can couple the obturators 150, while the second hub 220 can couple the anchoring legs 110. More specifically, the obturators 150 and/or the anchoring legs 110 can be coupled to the respective first and second hubs 210, 220 in a manner that allows the anchoring legs 110 and/or the obturators 150 to move, bend, or flex outward and/or inward. Relative movement of the first and second hubs 210, 220 can move the obturators 150 and the anchoring legs 110. As described above, relative movement of the obturators 150 and the anchoring legs 110 can reconfigure the filter 10c from the pre-deployed configuration to the deployed configuration and vice versa.

FIG. 6A illustrates the filter 10c in the deployed configuration, wherein the anchors 140 extend outward and away from the anchoring legs 110, such as to engage the wall of the body lumen. Hence, to reconfigure the filter 10c from the deployed configuration to the pre-deployed configuration, the first and/or second hubs 210, 220 can reduce the distance therebetween, thereby advancing the obturators 150 into the anchoring legs 110 and straightening out or collapsing the anchors 140. For example, the first hub 210 can be moved toward the second hub 220, while the second hub 220 may remain stationary. It should be appreciated that any number of suitable relative movements can bring the first and second hubs 210, 220 closer together.

The first and/or second hubs 210, 220 can have any number of suitable configurations. For example, the first and/or second hubs 210, 220 can have a ring-like shape, which can include a hollow or cored-out center. Alternatively, the first and/or second hubs 210, 220 can be plates, tubular structures, and may have any number of other suitable shapes and sizes.

Figure 6B:
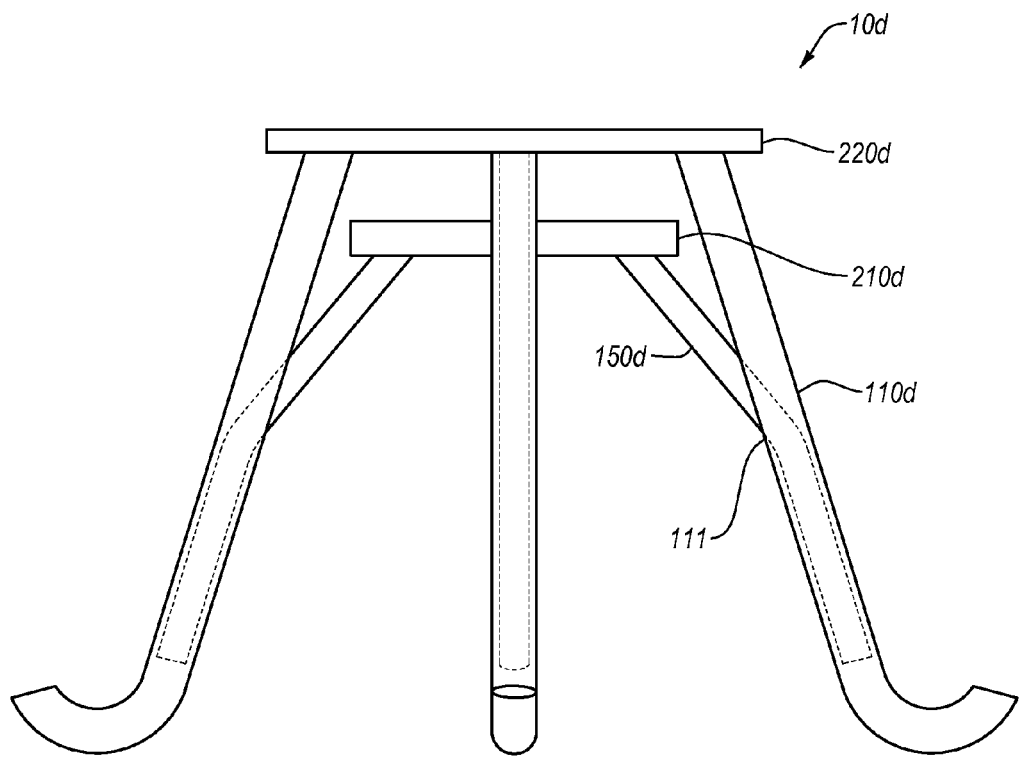
FIG. 6B illustrates a side view of a filter in accordance with another embodiment of the present invention.

In at least one embodiment, the first hub 210 can be closer to the proximal end of the filter 10c than the second hub 220. Such configuration may be preferable in some instances. It should be appreciated, however, that this disclosure is not so limited. FIG. 6B illustrates an embodiment of filter 10*d* that includes first and second hubs 210*d*, 220*d*, where the second hub 220*d* is closer to the proximal end of the filter 10*d* than the first hub 210*d*. Except as otherwise described herein, the filter 10*d* and its components and elements can be similar to or the same as any of the filters 10, 10*a*, 10*b*, 10*c* (FIGS. 1A-2B and 6A).

In one embodiment, anchoring legs 110*d* of the filter 10*d* can include one or more side ports 111, which can allow obturators 150*d* to pass therethrough and into the anchoring legs 110*d*. Accordingly, the obturators 150*d* can be coupled at the first hub 210*d*, while the anchoring legs 110*d* can be coupled at the second hub 220*d*. Consequently, relative movement of the first and second hubs 210*d*, 220*d* can reconfigure the filter 10*d* from the pre-deployed configuration to the deployed configuration and vice versa.

Figure 7A:
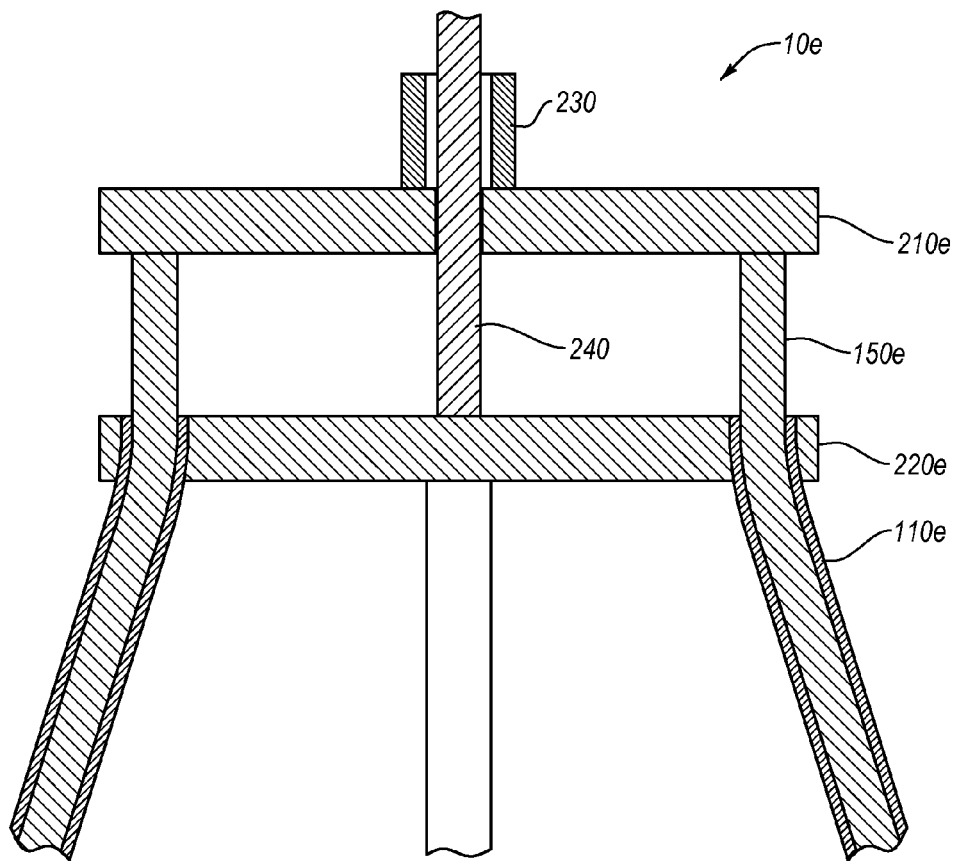
FIG. 7A illustrates a cross-sectional view of a filter in accordance with yet another embodiment of the present invention.

In some embodiments, the first and second hubs can be connected or coupled together. For example, the first and second hubs can be connected to an inner member of a catheter through a post mounted on each of the hubs, each post containing a connection mechanism, as described below in further detail. Several configurations of posts are possible; two illustrative embodiments are provided in FIGS. 7A-7B. More specifically, FIG. 7A shows a partial view of a filter 10*e*. Except as otherwise described herein, the filter 10*e* and its components and elements can be similar to or the same as any of the filters 10, 10*a*, 10*b*, 10*c*, 10*d* (FIGS. 1A-2B and 6A-6B).

In an embodiment, the filter 10*e* includes an outer post 230 that is connected to a first hub 210*e*, and an inner post 240 that is connected to a second hub 220*e*. The first and second hubs 210*e*, 220*e* can couple obturators 150*e* and anchoring legs 110*e*, respectively. As noted above, relative movement of the first and second hubs 210*e*, 220*e* can reconfigure the filter 10*e* from pre-deployed configuration to the deployed configuration and vice versa. In one embodiment, such movement can be actuated via the outer and inner posts 230, 240. More specifically, the inner and outer posts 230, 240 can couple to an inner member, which may be located in a catheter.

Accordingly, one or more inner members can be manipulated to produce relative movement of the first and second hubs 210*e*, 220*e*. In other words, the inner and outer posts 230, 240 can be coupled to one or more inner members in a manner that allows the inner members to move the inner and outer posts 230, 240 relative to each other. Furthermore, the inner and outer posts 230, 240 can include attachment mechanisms, which can allow the inner and/or outer posts 230, 240 to be operably coupled or secured to the inner member. Suitable connection mechanisms may include, but are not limited to a hook, an eyelet, a threaded end, a snare-receiver, a snap-clip, etc.

Figure 7B:
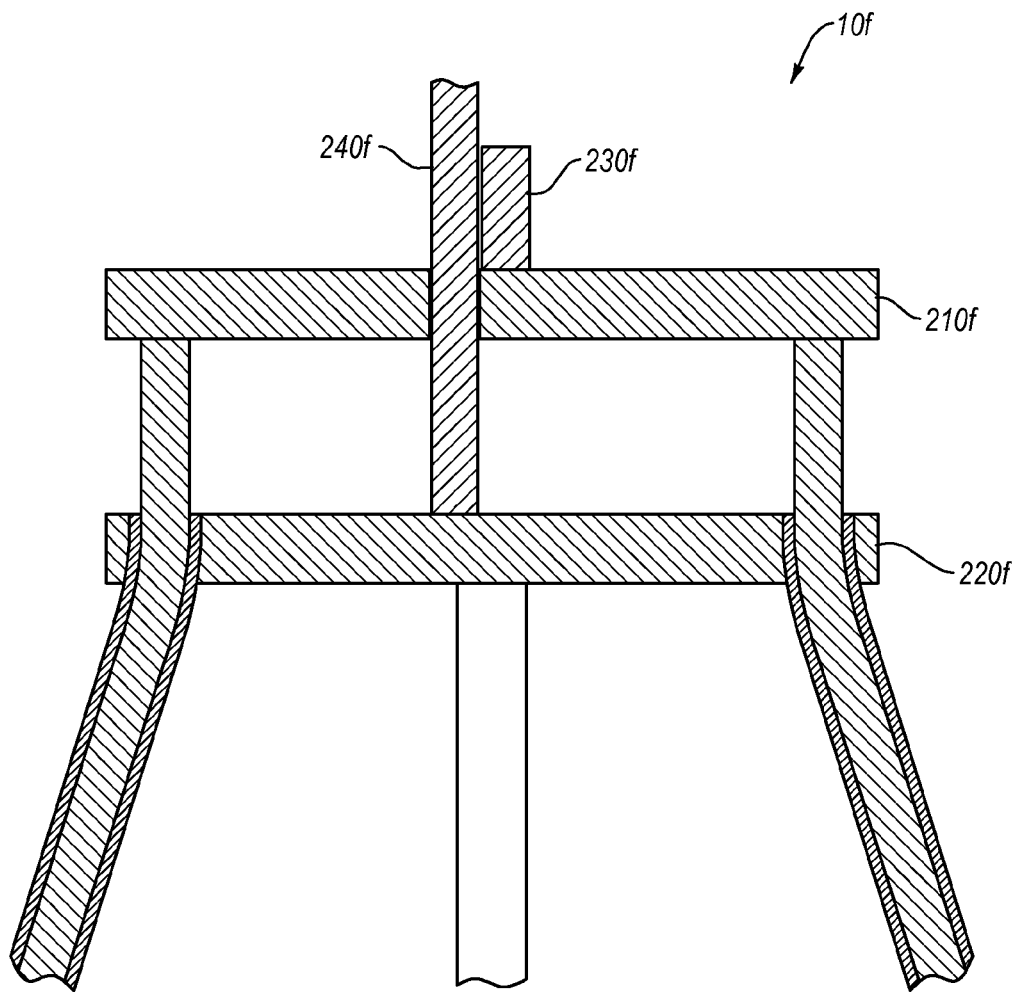
FIG. 7B illustrates a cross-sectional view of a filter in accordance with still one other embodiment of the present invention.

In additional or alternative embodiments, the first and second hubs can have adjacent or non-overlapping posts. For instance, as illustrated in FIG. 7B, a filter 10*f* include first and second posts 230, 240 coupled to respective first and second hubs 210*f*, 220*f*. Except as otherwise described herein, the filter 10*f* and its components and elements can be similar to or the same as any of the filters 10, 10*a*, 10*b*, 10*c*, 10*d*, 10*e* (FIGS. 1A-2B, 6A-6B, and 7A). In one example, the first and second posts 230*f*, 240*f* can be semi-circular posts and may be mounted in parallel. Other shapes, cross-sections, and configurations of the first and second posts 230*f*, 240*f* can be used and are within the scope of this disclosure.

In any event, the first and second posts 230*f*, 240*f* can couple to the inner members of a catheter in a manner that allows the inner members to mover the first and second posts 230*f*, 240*f* relative to each other. As mentioned above, relative movement of the first and second posts 230*f*, 240*f* can produce corresponding relative movement of the first and second hubs 210*f*, 220*f*, which can reconfigure the filter 10*f* from the pre-deployed configuration to the deployed configuration and vice versa.

Figure 8:
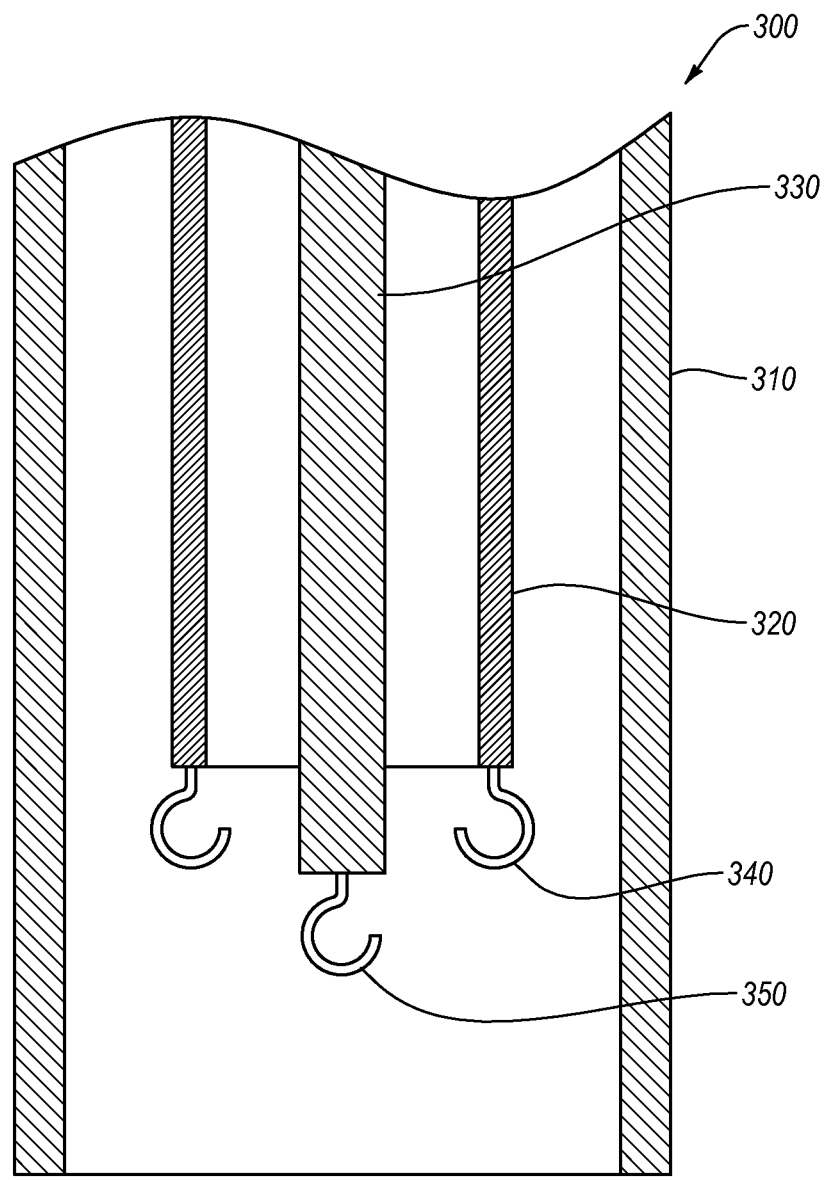
FIG. 8 illustrates a cross-sectional view of a catheter useable for delivery or retrieval of the filter in accordance with an embodiment of the present invention.

FIG. 8 shows a partial view of a catheter 300, according to one embodiment of the present invention, which can be used to introduce and/or retrieve the filter. More specifically, FIG. 8 illustrates the distal end of the catheter 300. The catheter 300 includes an outer sheath 310, which may be dimensioned to contain the filter (i.e., any of the filters 10, 10*a*, 10*b*, 10*c*, 10*d*, 10*e*, 10*f* (FIGS. 1A-2B, 6A-6B, and 7A-7B)).

The catheter 300 also can include a first inner member 320 and a second inner member 330, which may be located inside of the catheter 300. In some instances, the first and second inner members 320, 330 can be located coaxially with each other and/or with the outer sheath 310. The first inner member 320 can contain one or more hooks 340, which may connect or couple the first inner member 320 to one or more posts connected to a hub of the filter, as described below in more detail. Similarly, the second inner member 330 contains a hook 350 that can connect the second inner member 330 to another hub post. Hence, movement of the first and second inner members 320, 330 can be translated to the movement of the hubs of the filter, which can reconfigure the filter from the pre-deployed configuration to the deployed configuration, and the reverse, in a manner described above.

Although the first and second inner members 320, 330 are described as cylindrical elongate members with hook-like connectors, it should be appreciated that the first and second inner members 320, 330 can have other shapes, cross-sections, configurations and attachment mechanisms. Furthermore, the first and second inner members 320, 330 can be positioned adjacent to one another, without overlapping. For example, the first and second inner members 320, 330 can extend next to each other along the length of the catheter 300.

Movement between the obturators and/or the anchoring legs can be achieved in a variety of ways, including longitudinal movement of the first and second inner members 320 and 330 with respect to each other. Alternatively, two coaxial inner members can manipulate or actuate two coaxial posts that have a threaded connection, by a rotation and screwing or unscrewing of one inner member with respect to the other inner member.

Generally, to deliver and/or retrieve the filter, the filter can be moved into or out of a catheter, and the obturators can be moved with respect to the anchoring legs (or vice versa). Hence, an embodiment includes a filtering system that can include an outer sheath which can contain or accommodate the filter. The catheter also may include one or more inner members connected to hubs that can actuate or more the anchoring legs and/or obturators. The ability to move the outer sheath and/or the inner members independently can allow an operator to move the entire device, anchoring legs, and obturators independently.

Figure 9:
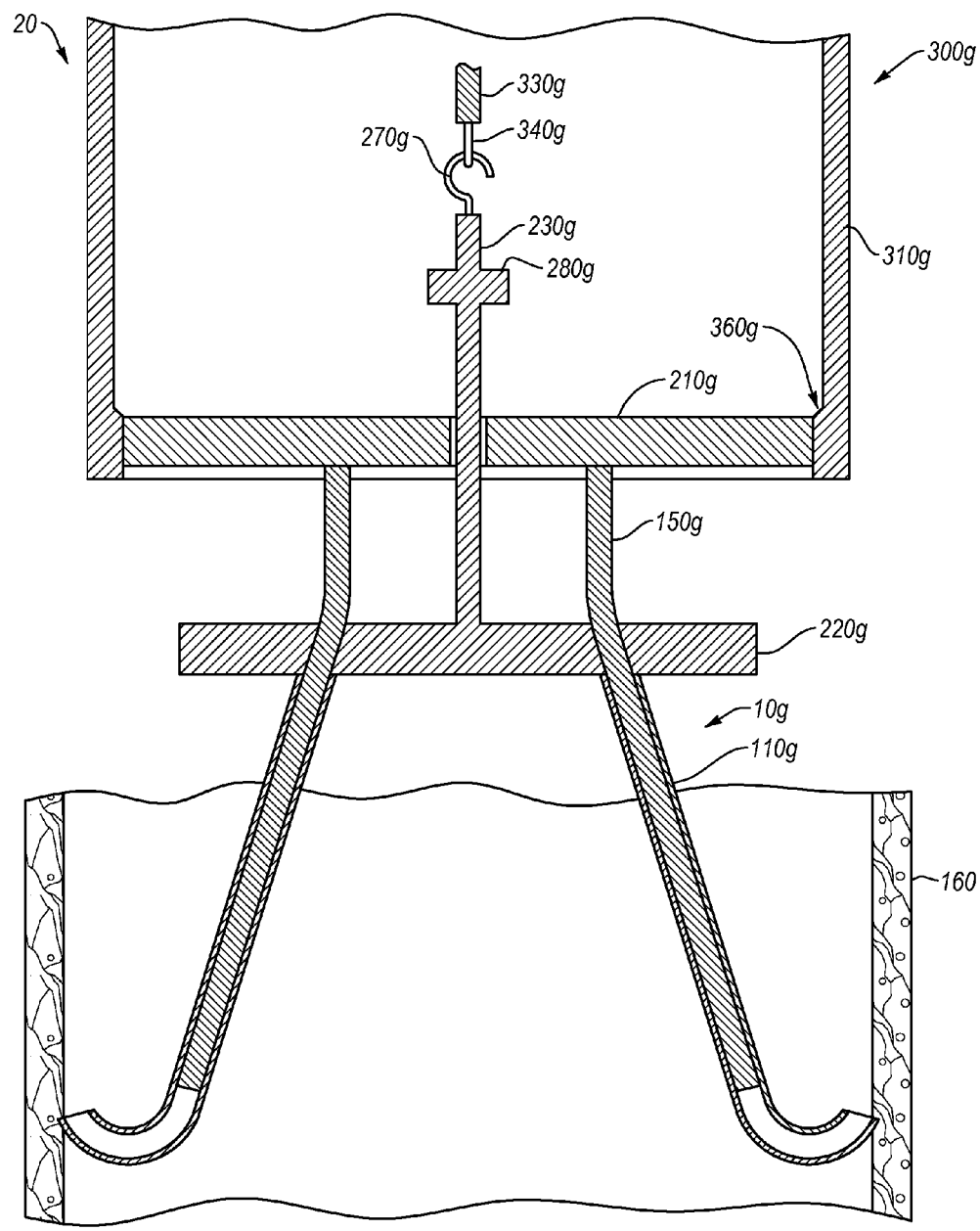
FIG. 9 illustrates a cross-sectional view of a filtering system in accordance with an embodiment of the present invention.

FIG. 9 illustrates an embodiment of a filtering system 20. The filtering system 20 can include a filter 10*g* coupled to a single inner member 330*g*. The filter 10*g*, including a filtering section 100*g* and an operator section 200*g*, can be contained inside the catheter 300*a*. The filter 10*g* and its components and elements can be similar to or the same as any of the filters 10a, 10b, 10c, 10d, 10e, 10f (FIGS. 1A-2B, 6A-6B, and 7A-7B)). For instance, the filter 10g includes first and second hubs 210g, 220g, which can couple to the inner member 330g, as described below.

In one embodiment, the first hub 210g can be located closer to the proximal end of the catheter (e.g., closer to the user) and near the second hub 220g. Also, the first hub 210g can have a larger perimeter (e.g., a larger circumference) than the second hub 220g. An outer sheath 310g of the catheter 300g can have an internal rim 360g, which may have an inner circumference that can provide friction fit or interference with the outer circumference of the first hub 210g, but which can allow the second hub 220g to move freely. In other words, the internal rim 360g can impede movement of the first hub 210g, while allowing the second hub 220g to pass freely or unimpeded.

In one embodiment, the second hub 220g can be coupled to a post 230. The post 230g can pass through the first hub 210g in a manner that the post 230g can move freely relative to the first hub 210g. In addition, the inner member 330g can be connected to the post 230g (e.g., via a hook 270 and an eyelet 340g connection).

Accordingly, the inner member 330g can move the post 230g together with the second hub 220g in the proximal and/or distal direction. Movement of the second hub 220g in the distal direction can move anchoring legs 110g of the filter 10g in the distal direction. Conversely, moving the second hub 220g in the proximal direction can move the anchoring legs 110g in the proximal direction.

The first hub 210g can secure obturators 150g of the filter 10g. Thus, relative movement of the first and second hubs 210g, 220g can produce relative movement of the anchoring legs 110g and obturators 150g, which can reconfigure the filter 10g from pre-deployed configuration into the deployed configuration and vice versa. As described above, movement of the first hub 210g can be impeded by the internal rim 360g of the catheter 300g. More specifically, when the first hub 210g is advanced in the distal direction, the friction and/or interference between the internal rim 360g and the first hub 210g can impede movement of the first hub 210g. Consequently, when the inner member 330g is advanced in the distal direction and moves the second hub 220g, the internal rim 360g can hold the first hub 210g substantially stationary relative to the second hub 200g, thereby moving the obturators 150g out of the anchoring legs 110g. As mentioned above, in one embodiment, moving the obturators 150g out of the anchoring legs 110g can reconfigure the anchoring legs 110g and the filter 10g into the deployed configuration, in which the filter 10g is anchored to the wall of the body lumen 160.

The post 230g also can include a stop 280g. Thus, when as the post 230g moves through the first hub 210g in the distal direction, the stop 280g can prevent further movement of the post 230g. Moreover, further movement of the inner member 330g in the distal direction can apply pressure through the stop 280g onto the first hub 210g, thereby pushing the first hub 210g out of the outer sheath 310g.

Similarly, when the inner member 330g moves in the proximal direction, the post 230g together with the second hub 220g can move in the proximal direction. As the anchoring legs 110g move in the proximal direction, the anchoring legs 110g may push onto the obturators 150g. In some embodiment, because the obturators 150g together with the first hub 210g may be free to move in the proximal direction, the anchoring legs 110g may not be forced onto the obturators until movement of the first hub 210g is impeded by the internal rim 360g. Accordingly, as the internal rim 360g impedes movement of the first hub 210g (and, thus, movement of the obturators 150g) in the proximal direction, the anchoring legs 110g can be pulled onto the obturators 150g, as the inner member 330g continues to move the second hub 220g in the proximal direction together with the anchoring legs 110g, thereby reconfiguring the filter 10g into the pre-deployed configuration. In other words, the inner member 330g can move in the proximal direction to collapse the filter 10g into the pre-deployed configuration. Conversely, the inner member 330g can move in the distal direction to expand the filter 10g into the deployed configuration.

In one or more embodiments, the catheter 300g can be advanced into the blood vessel and to a desired location therein. Subsequently, the outer sheath 310g of the catheter 300g can be withdrawn proximally, while the filter 10g may be held substantially stationary with the inner member 330g of the catheter 300g. In other words, the catheter 300g can be moved relative to the filter 10g to reconfigure the filter 10g into the deployed and pre-deployed configurations.

During the implantation period of the filter, thrombus and tissue accumulation may occur around the anchors, which may require a force to bring the anchors into a retrieval or pre-deployed configuration that is larger than the force needed for deployment of the filter. In such case, a retrieval catheter with two inner members can be used to retrieve the filter.

Figure 10:
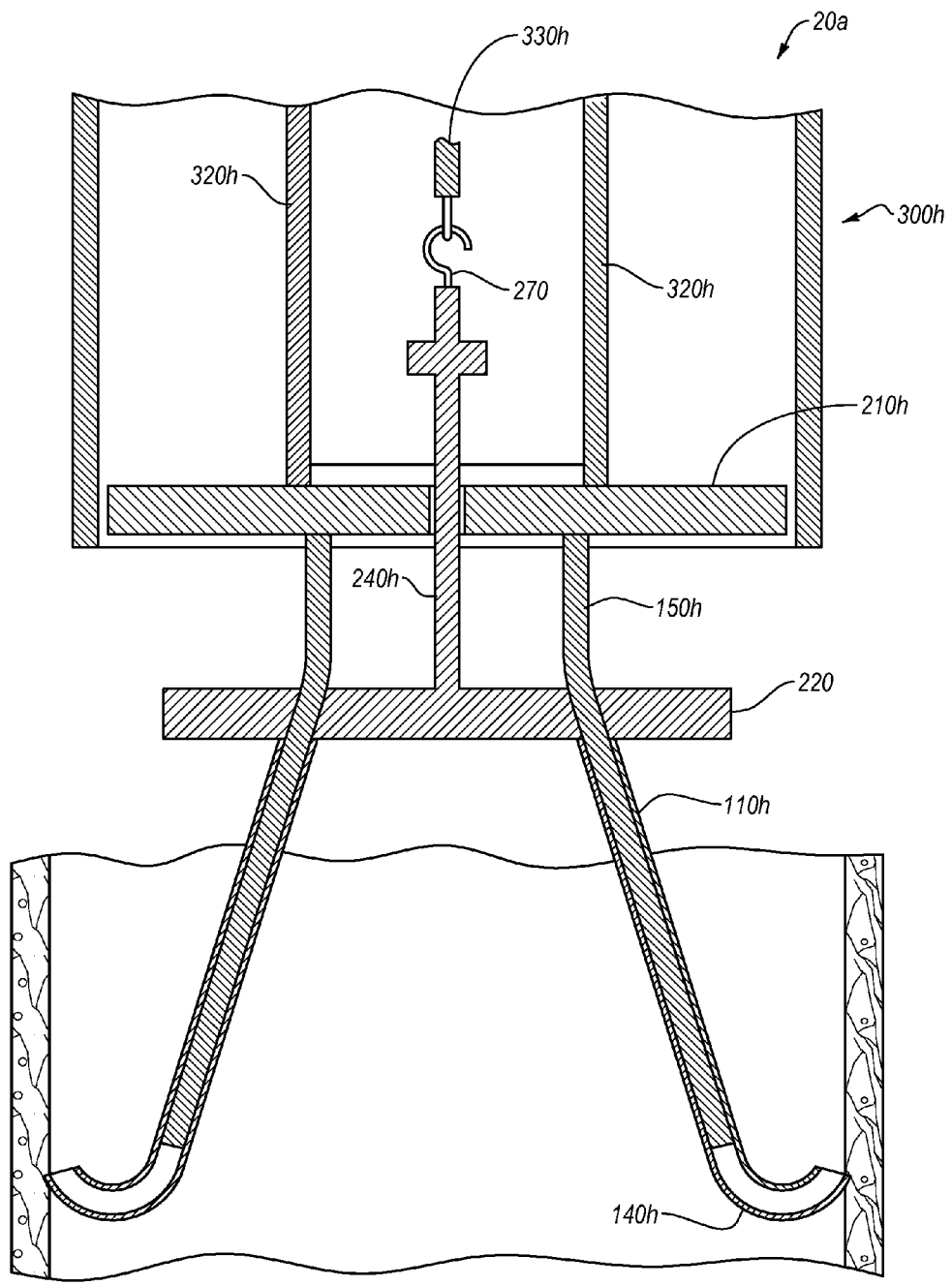
FIG. 10 illustrates a cross-sectional view of a filtering system in accordance with another embodiment of the present invention.

FIG. 10 illustrates one embodiment of a filtering system 20a. The filtering system 20a and its components and elements can be similar to or the same as the filtering system 20 (FIG. 9) and its respective components and elements. For instance, the filtering system 20a can include a catheter 300h which can have a first inner member 320h connected to the first hub 210h. The first hub 210h can be coupled to one or more obturators 150h.

The first inner member 320h can have sufficient rigidity to be able to push and provide sufficient force against the first hub 210h. No hook or other specific attachment to the first hub 210h may be necessary since, in one embodiment, only a distal or pushing action is required. Alternatively, in an embodiment, the first inner member 320h can be directly or indirectly (e.g., via a post) coupled to the first hub 210h, such that the first inner member 320h can push and/or pull the first hub 210h.

To move the first hub 210h distally with respect to the second hub 220h, a post 240h coupled to the second hub 220h may be connected to a second inner member 330h by a hook 270 and an eyelet 340. The second hub 220h can be held substantially stationary. Then, a distal force can be exerted on the first hub 210h by pushing the first inner member 320h distally, thus moving the obturators 150h distally relative to the anchoring legs 110h, to bring the anchors 140 in a non-anchoring or pre-deployed configuration.

Accordingly, embodiments of the present invention involve an implantable and retrievable filter for use in a body lumen. The filter can include one or more first anchoring legs having a pre-deployed, non-anchoring configuration and a deployed, anchoring configuration. Each of the one or more first anchoring legs in the deployed, anchoring configuration may have a first anchor sized and configured to anchor the filter within the body lumen. Additionally, the filter may include one or more first obturators movable inside the one or more first anchoring legs from a first position to a second position. Furthermore, the one or more first anchoring legs may be in the pre-deployed non-anchoring configuration when the one or more first obturators are in the first position. Similarly, the one or more first anchoring legs may be in the deployed, anchoring configuration when the one or more first obturators are in the second position.

Embodiments of the present invention also may include a filtering system for deployment in a body lumen. Such system may have a filter that includes at least one anchoring leg reconfigurable between a pre-deployed, non-anchoring configuration, and a deployed, anchoring configuration. The at least one anchoring leg may form one or more anchors sized and configured to anchor the filter within the body lumen. In addition, the system may include at least one obturator. The at least one anchoring leg and the at least one obturator may be movable relative to each other between a first position and a second position. In the first position, the at least one anchoring leg may be in the pre-deployed, non-anchoring configuration, and in the second position, the at least one anchoring leg may be in the deployed, anchoring configuration. The system also may have a catheter that includes an outer sheath sized and configured to house the filter therein. The catheter also may include one or more inner members coupled to one or more of the at least one anchoring leg and the at least one obturator. The one or more inner members may be movable to position the at least one anchoring leg and the at least one obturator at one or more of the first position and the second position.

Embodiments described herein also may involve a method of removably implanting a filter in a body lumen. Such the method may include positioning the filter inside the body lumen, and expanding one or more anchoring legs into a partially-deployed configuration, the one or more anchoring legs being positioned near a wall of the body lumen in the partially-deployed configuration. The method may also include moving one or more of the one or more anchoring legs and one or more obturators from a first position to a second position, the one or more obturators being movable inside the one or more anchoring legs. Furthermore, the method may include reconfiguring the one or more anchoring legs into the deployed configuration, each of the one or more anchoring legs forming one or more anchors that engage the anchoring legs with a wall of the body lumen.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

What is claimed is:

1. An implantable and retrievable filter for use in a body lumen, the filter comprising:
   one or more first anchoring legs having a pre-deployed, non-anchoring configuration, and a deployed, anchoring configuration, wherein each of the one or more first anchoring legs in the deployed, anchoring configuration has a first anchor sized and configured to anchor the filter within the body lumen;
   one or more first obturators movable inside the one or more first anchoring legs from a first position to a second position, the second position being proximal the first position; and
   wherein:
   the one or more first anchoring legs are in the pre-deployed non-anchoring configuration when the one or more first obturators are in the first position; and
   the one or more first anchoring legs are in the deployed, anchoring configuration when the one or more first obturators are in the second position that is proximal the first position.

2. The filter as recited in claim 1, wherein the first anchor is formed by a distal end of the one or more first anchoring legs.

3. The filter as recited in claim 2, wherein in the second position, the one or more first obturators are moved out of the distal end of the first anchoring leg, thereby allowing the distal end of each of the one or more first anchoring legs to form the first anchor.

4. The filter as recited in claim 2, further comprising:
   one or more second anchoring legs having a pre-deployed, non-anchoring configuration, and a deployed, anchoring configuration, wherein each of the one or more second anchoring legs in the deployed, anchoring configuration has a second anchor sized and configured to anchor the filter within the blood vessel, the second anchor being located along a length of the one or more second anchoring legs; and
   one or more second obturators movable inside the one or more second anchoring legs to reconfigure the one or more second anchoring legs between the pre-deployed, non-anchoring configuration and the deployed, anchoring configuration.

5. The filter as recited in claim 4, wherein a portion of a wall of each of the one or more second anchoring legs forms the second anchor.

6. The filter as recited in claim 1, wherein the first anchor is located along a length of the one or more first anchoring legs.

7. The filter as recited in claim 6, wherein in the second position, the one or more first obturators push a portion of a wall of each of the one or more first anchoring legs, the portion of the wall of each of the one or more first anchoring legs forming the first anchor.

8. The filter as recited in claim 1, further comprising a first hub that couples together the one or more first obturators.

9. The filter as recited in claim 8, further comprising a second hub that couples together the one or more first anchoring legs.

10. The filter as recited in claim 1, further comprising one or more positioning legs.

* * * * *